(12) United States Patent
Ammann et al.

(10) Patent No.: US 7,612,209 B2
(45) Date of Patent: Nov. 3, 2009

(54) PSEUDO PROLINE DIPEPTIDES

(75) Inventors: Thomas Ammann, Muttenz (CH); Stephan Goetzoe, Muttenz (CH); Bernd Thern, Basel (CH); Sandra Welz, Neuenburg (DE); Klaus-Juergen Wolter, Muellheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 316 days.

(21) Appl. No.: 11/818,608

(22) Filed: Jun. 14, 2007

(65) Prior Publication Data

US 2008/0004451 A1 Jan. 3, 2008

(30) Foreign Application Priority Data

Jun. 28, 2006 (EP) .................... 06116238

(51) Int. Cl.
*C07D 263/04* (2006.01)
(52) U.S. Cl. .................................... 548/215
(58) Field of Classification Search ........... 548/215
See application file for complete search history.

(56) References Cited

FOREIGN PATENT DOCUMENTS

WO WO 86/04334 A1 7/1986

OTHER PUBLICATIONS

Wöhr et al., J. Am. Chem. Soc., 118, pp. 9218-9227 (1996).
Green, T., "Protective Groups in Organic Synthesis", Chapter 7, John Wiley and Sons, Inc., pp. 309-385 (1991).
Green, T., "Protective Groups in Organic Synthesis", Chapter 2, John Wiley and Sons, Inc., pp. 10-142 (1991).

*Primary Examiner*—Golam M Shameem
(74) *Attorney, Agent, or Firm*—George A. Johnston; Dennis P. Tramaloni; Brian C. Remy

(57) ABSTRACT

Disclosed is a process for the manufacture of pseudo proline dipeptides of the formula

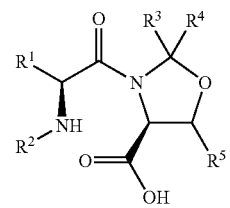

wherein $R^1$ is a side chain of an alpha amino acid, $R^2$ is an amino protecting group and $R^3$ and $R^4$ are independently either hydrogen or $C_{1-4}$-alkyl, and $R^5$ is hydrogen or methyl starting from an amino acid derivative of the formula

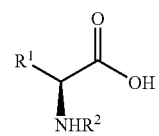

wherein $R^1$ and $R^2$ are as defined above. Pseudo proline dipeptides can be used as reversible protecting groups for Ser, Thr and Cys and thus are versatile tools in peptide chemistry.

15 Claims, No Drawings

PSEUDO PROLINE DIPEPTIDES

PRIORITY TO RELATED APPLICATION(S)

This application claims the benefit of European Patent Application No. 06116238.4, filed Jun. 28, 2006, which is hereby incorporated by reference in its entirety.

BACKGROUND OF THE INVENTION

The invention relates to a novel process for the manufacture of the compounds of formula I:

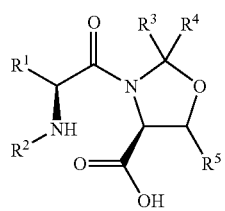

wherein $R^1$-$R^5$ are as defined in the detailed description and in the claims.

The pseudo proline dipeptides of formula I can be used as reversible protecting groups for Ser, Thr, and Cys and prove to be versatile tools for overcoming some intrinsic problems in the field of peptide chemistry [JACS 1996, 118, 9218-9227]. The presence of ΨPro within a peptide sequence results in the disruption of β-sheet structures considered as a source of intermolecular aggregation. The resulting increased salvation and coupling kinetics in peptide assembly such as Fmoc solid phase peptide synthesis facilitates chain elongation especially for peptides containing "difficult sequences".

SUMMARY OF THE INVENTION

The present invention provides a short and technically feasible process for synthesizing the pseudo proline dipeptides of formula I:

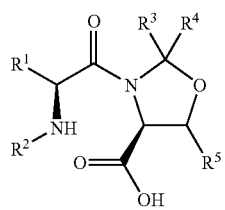

wherein $R^1$-$R^5$ are as defined in the detailed description and in the claims;

comprising the steps of: (a) reacting an amino acid derivative of formula II as defined herein with serine or threonine to obtain a dipeptide of formula III as defined herein; (b) adding the amine of formula V as defined herein to form the ammonium salt of the dipeptide of formula III in crystal form; (c) adding an acid to the ammonium salt in step (b) to release the free acid of the dipeptide of formula III from the ammonium salt, and removing the protonated amine from the reaction mixture; and (d) effecting the ring closure of the free acid of the dipeptide of formula III in step (c) with a certain compound as defined herein in the presence of an acidic catalyst to obtain the compounds of formula I.

This process provides a high yield of the product without any chromatographic purification step.

DETAILED DESCRIPTION OF THE INVENTION

In detail, the present invention provides a process for the manufacture of the compounds of formula I:

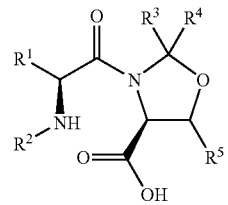

wherein: (1) $R^1$ is a side chain of an alpha amino acid, (2) $R^2$ is an amino protecting group, (3) $R^3$ and $R^4$ are independently either hydrogen or a $C_{1-4}$-alkyl, and (4) $R^5$ is hydrogen or methyl;

wherein said process comprises the following steps:

(a) reacting an amino acid derivative of formula II:

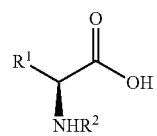

wherein $R^1$ and $R^2$ are as defined previously, with serine or threonine to obtain a dipeptide of formula III:

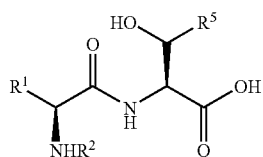

wherein $R^1$, $R^2$ and $R^5$ are as defined previously;

(b) adding the amine of formula V:

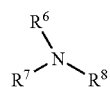

wherein $R^6$, $R^7$ and $R^8$ are independently selected from the group consisting of hydrogen, a $C_{1-4}$-alkyl and a $C_{3-7}$-cycloalkyl, with the proviso that not all of $R^6$, $R^7$ and $R^8$ are hydrogen;

to form the ammonium salt of the dipeptide of formula III in crystal form:

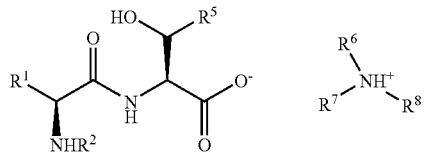

wherein $R^1$, $R^2$, $R^5$, $R^6$, $R^7$ and $R^8$ are as defined previously;

(c) adding an acid to the ammonium salt in step (b) to release the free acid of the dipeptide of formula III from the ammonium salt, and removing the protonated amine from the reaction mixture; and (d) effecting the ring closure of the free acid of the dipeptide of formula III in step (c) with a compound selected from the group consisting of:

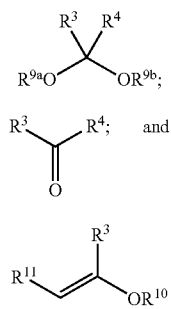

wherein: (1) $R^3$ and $R^4$ are independently either hydrogen or a $C_{1-4}$-alkyl, with the proviso that not both $R^3$ and $R^4$ are hydrogen, (2) $R^{9a}$ and $R^{9b}$ are independently a $C_{1-4}$-alkyl, (3) $R^{10}$ is a $C_{1-4}$-alkyl, a $C_{1-4}$-alkanoyl or an aryl, and (4) $R^{11}$ is hydrogen or a $C_{1-3}$-alkyl, in the presence of an acidic catalyst to obtain the compounds of formula I.

It is further understood that the serine or threonine can be used either in its L- or D-configuration, as racemates, or in various mixtures of their isomers. Preferably the L-configuration is used.

The term "$C_{1-4}$-alkyl" refers to a branched or straight-chain monovalent saturated aliphatic hydrocarbon radical of one to four carbon atoms. This term is further exemplified by radicals such as methyl, ethyl, n-propyl, isopropyl, n-butyl, s-butyl and t-butyl.

The term "$C_{3-7}$-cycloalkyl" refers to a cycloalkyl group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono-substituted or multiply-substituted by halogen, hydroxy, CN, $CF_3$, $NO_2$, $NH_2$, N(H,alkyl), N(alkyl)$_2$, carboxy, aminocarbonyl, alkyl, alkoxy, aryl and/or aryloxy. A preferred aryl group is phenyl.

The term "alkanoyl" relates to a $C_{1-4}$-alkyl carbonyl group. Examples include acetyl, n-propanoyl, isopropanyl, n-butanoyl, s-butanoyl and t-butanoyl, preferably acetyl.

The term "side chain of an amino acid" used in connection with the $R^1$ substituent refers to side chains of the alpha amino acids selected from the group consisting of valine, leucine, isoleucine, methionine, phenylalanine, asparagine, glutamine, glutamic acid, histidine, lysine, arginine, aspartic acid, alanine, serine, threonine, tyrosine, tryptophan, cysteine, glycine, aminoisobutyric acid, and proline. For side chains of amino acids which carry a hydroxy group the hydroxy group is optionally protected by a hydroxy protecting group as defined below. For side chains that carry additional amino groups the amino group is optionally protected by an amino protecting group as defined below.

In certain preferred embodiments, $R^1$ is preferably a side chain of an amino acid selected from the group consisting of: valine, leucine, isoleucine, phenylalanine, asparagine, glutamine, glutamic acid, lysine, aspartic acid, alanine, serine, threonine, tyrosine, and tryptophan; more preferably serine and threonine.

The term "amino protecting group" refers to any substituents conventionally used to hinder the reactivity of the amino group. Suitable amino protecting groups are described in Green T., "Protective Groups in Organic Synthesis", Chapter 7, John Wiley and Sons, Inc., 1991, 309-385. Suitable amino protecting groups are Fmoc, Cbz, Moz, Boc, Troc, Teoc and Voc. A preferred amino protecting group is Fmoc.

The term "hydroxy protecting group" refers to any substituents conventionally used to hinder the reactivity of the hydroxy group. Suitable hydroxy protecting groups are described in Green T., "Protective Groups in Organic Synthesis", Chapter 1, John Wiley and Sons, Inc., 1991, 10-142. Suitable hydroxy protecting groups are t-butyl, benzyl, TBDMS and TBDPS. A preferred hydroxy protecting group is t-butyl.

The meaning of certain abbreviations as used herein is provided in the following table:

| | |
|---|---|
| Fmoc | 9-Fluorenylmethoxycarbonyl- |
| Boc | t-Butoxycarbonyl- |
| Cbz | Carbobenzyloxy |
| Z | Benzyloxycarbonyl |
| tBU | t-Butyl |
| Moz | p-Methoxybenzyloxycarbonyl |
| Troc | 2,2,2-Trichloroethoxycarbonyl |
| Teoc | 2-(Trimethylsilyl)ethoxycarbonyl |
| Voc | Vinyloxycarbonyl |
| TBDMS | t-Butyldimethylsilyl ether |
| TBDPS | t-Butyldiphenylsilyl ether |
| HBTU | O-Benzotriazole N,N,N',N'-tetramethyl-uronium-hexafluoro-phosphate |
| HOBt | 1-Hydroxybenzotriazole |
| HOSu | N-Hydroxysuccinimide |
| EDC | (3-Dimethylamino-propyl)-ethyl-carbodiimide (hydrochloride) |
| DIC | N,N'-Diisopropylcarbodiimide |
| DCC | N,N'-Dicyclohexylcarbodiimide |

Step (a)

In the first step (a) an amino acid derivative of the formula II:

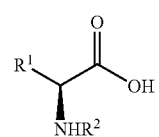

wherein $R^1$ and $R^2$ are as defined previously reacted with serine or threonine and the resulting dipeptide is crystallized as an ammonium salt of formula III:

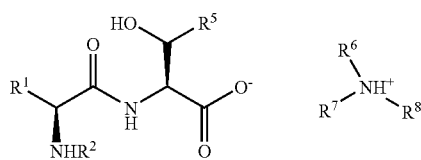

wherein $R^1$, $R^2$, $R^5$, $R^6$, $R^7$ and $R^8$ are as above.

The amino acid derivatives of formula II are as a rule commercially available compounds. Suitable amino acid derivatives of formula II include, according to the preferences given for $R^1$ and $R^2$, Fmoc-L-Ser(tBu)-OH and Fmoc-L-Thr(tBu)-OH.

Prior to the coupling with serine or threonine, the amino acid derivative of formula II is expediently activated with an activating reagent.

Suitable activating reagents can be selected from the group consisting of: DIC/HOSu, DIC/Pentafluorphenol, DIC/HOBt, DCC/HOSu, DCC/Pentafluorophenol, DCC/HOBt, EDC(xHCl)/HOSu, and HBTU/HOBt. A preferred coupling agent is DIC/HOSu. The DIC is usually used in an amount of 1.0 to 1.4 equivalents and the HOSu is usually used in an amount of 1.0 to 1.8 equivalents related to one equivalent of the amino acid derivative of formula I.

As a rule the activation reaction is performed in the presence of a suitable organic solvent, such as ethylacetate, N,N-dimethylformamide, acetone or tetrahydrofuran, preferably ethylacetate at a temperature of –5° C. to 25° C.

The coupling with serine or threonine, preferably with L-serine or L-threonine, can then be performed at a temperature of 10° C. to 30° C. in the presence of an organic solvent, such as ethylacetate, acetone or tetrahydrofuran or mixtures thereof with water. A preferred solvent is a mixture of acetone and water.

The ratio serine or threonine to amino acid derivative of formula II is usually selected in the range of 1.5 to 3.0 to 1, preferably 2.0 to 1. The pH of the reaction mixture is expediently set at a value of 7.5 to 9.0.

Step (b)

In step (b) the formation of the ammonium salt of formula III happens by adding to the dipeptide previously formed an amine of formula V:

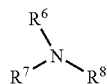

V wherein $R^6$, $R^7$ and $R^8$ are independently selected from the group consisting of hydrogen, a $C_{1-4}$-alkyl, and a $C_{3-7}$-cycloalkyl, with the proviso that not all of $R^6$, $R^7$ and $R^8$ are hydrogen. Suitable amines of formula V are those wherein $R^6$, $R^7$ and $R^8$ are independently selected from the group consisting of hydrogen, ethyl and cyclohexyl, with the proviso that not all $R^6$, $R^7$ and $R^8$ are hydrogen. Cyclohexylamine, dicyclohexylamine and triethylamine are the preferred amines; wherein dicyclohexylamine is the most preferred amine of formula V. The crystallization is commonly effected in suitable organic solvents such as lower alcohols like methanol, ethanol, n-propanol or i-propanol or in ethylacetate or tetrahydrofuran. A preferred solvent is ethanol.

The ammonium salts of formula III have previously not been described and thus are a further embodiment of the present invention.

Preferred ammonium salts are the dicyclohexylammonium salts of formula III wherein $R^1$ and $R^2$ are as described above, $R^5$ is hydrogen or methyl, $R^6$ is hydrogen and $R^7$ and $R^8$ are cyclohexyl.

More preferred are the compounds of formula III wherein:

a) $R^1$ stands for the L-serine side chain with O-tBu protection, $R^2$ is Fmoc, $R^5$ is H, $R^6$ is hydrogen and $R^7$ and $R^8$ are cyclohexyl.

b) $R^1$ stands for the L-serine side chain with O-tBu protection, $R^2$ is Fmoc, $R^5$ is methyl, $R^6$ is hydrogen and $R^7$ and $R^8$ are cyclohexyl.

c) $R^1$ stands for the L-threonine side chain with O-tBu protection, $R^2$ is Fmoc, $R^5$ is H, $R^6$ is hydrogen and $R^7$ and $R^8$ are cyclohexyl.

d) $R^1$ stands for the L-threonine side chain with O-tBu protection, $R^2$ is Fmoc, $R^5$ is methyl, $R^6$ is hydrogen and $R^7$ and $R^8$ are cyclohexyl.

Step (c)

In subsequent step (c) the free acid of the dipeptide is released in the presence of an acid and the protonated amine of formula V is removed by extraction. Particularly the free acid of the ammonium salt of formula III is released in the presence of a mineral acid, taken up in an organic solvent while the amine is removed by extraction with water and/or an aqueous solution of a mineral salt.

Suitable mineral acids are aqueous sulfuric acid or aqueous HCl, preferably aqueous sulfuric acid. Suitable organic solvents for taking up the free acid can be selected from the group consisting of: ethylacetate, t-butyl methyl ether, and methylenechloride. t-Butyl methyl ether has been found to be the preferred solvent.

The organic phase containing the free acid is as a rule washed several times with water and/or an aqueous solution of a mineral salt, like sodium chloride in order to completely remove the amine.

Step (d)

In step (d) the ring closure of the free acid of the dipeptide obtained in step (c) is effected with a compound selected from the group consisting of:

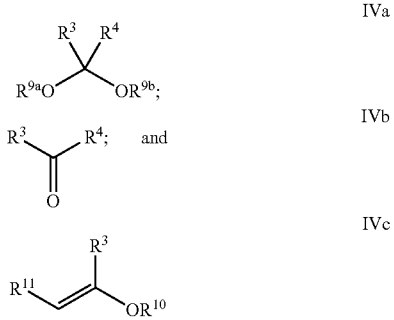

wherein $R^3$ and $R^4$ are independently either hydrogen or $C_{1-4}$-alkyl, with the proviso that not both $R^3$ and $R^4$ are hydrogen; $R^{9a}$ and $R^{9b}$ independently are a $C_{1-4}$-alkyl; $R^{10}$ has the meaning of a $C_{1-4}$-alkyl, a $C_{1-4}$-alkanoyl, or an aryl; and $R^{11}$ is hydrogen or $C_{1-3}$-alkyl, in the presence of an acidic catalyst.

Preferably the ring closure is effected with compounds of the formula IVa and IVc, and more preferably with the compounds selected from the group consisting of: 2,2-dimethoxypropan, 2-methoxypropen and 2-acetoxypropen, whereby 2,2-dimethoxypropan is the most preferred compound.

Ideally the compounds of formula IV are used in an amount of 6.0 to 16.0 equivalents, preferably 7.0 to 10.0 equivalents in relation to the dipeptide obtained in step (c).

Suitable acidic catalysts are selected from the group consisting of: methane sulfonic acid, (+) camphor-10-sulfonic acid, p-toluenesulfonic acid, and pyridinium p-toluenesulfonate, most preferably methane sulfonic acid. The acidic catalyst is usually applied in an amount of 0.05 to 0.30 equivalents, preferably 0.10 to 0.20 equivalents in relation to the dipeptide obtained in step (c).

The ring closure is effected in the presence of an organic solvent, such as in tetrahydrofuran, methylenechloride or toluene, preferably in tetrahydrofuran at reflux temperature.

Isolation and work up of the target product can be performed by using methods which are known to the skilled in the art.

The following examples illustrate the invention without limiting it.

EXAMPLES

Example 1

A 1000 mL double jacketed glass reactor equipped with a mechanical stirrer, a Pt-100 thermometer, reflux condenser, a dropping funnel and a nitrogen inlet was charged with 25 g (64.9 mmol) of Fmoc-L-Ser(tBu)-OH (1), 9.66 g (83.1 mmol) of N-hydroxysuccinimide and 180 mL of ethyl acetate. The resulting suspension was cooled to 0° C. A solution of 10.49 g (83.1 mmol) of diisopropyl carbodiimide in 20 mL of ethyl acetate was added within 15 minutes. The resulting mixture was stirred at 0° C. for 2 h and then for another hour at room temperature and sampled. The solvent was completely removed under reduced pressure (ca. 220 mbar) at a jacket temperature of maximal 50° C. The residue was treated with 250 mL of acetone at an internal temperature of 35° C. to 40° C., cooled to 20° C. and treated with 13.5 mL of water. The pH was set with 1.0 mL of 1 M HCl to pH 2-3 and the resulting mixture was stirred for 12 h at 20° C. and sampled. The suspension was then cooled to −5° C. to 0° C. and stirred for 1 h at this temperature. The precipitate was filtered off and the reactor and filter was rinsed with 50 mL of cold acetone (0° C.). The clear and colorless filtrate was added at 20° C. within 60 minutes to a solution of 13.57 g (127.8 mmol) of L-serine and of 13.63 g (257 mmol) of sodium carbonate in 122.5 ml of water. The resulting mixture was stirred for 1 h at 20° C. and sampled. The pH was set with 28 g of HCl (37%) to pH 2-3 and the organic solvent was removed under reduced pressure (<250 mbar) at a jacket temperature of maximal 50° C. The resulting suspension was treated at 35° C. to 40° C. with 125 mL of ethyl acetate and the resulting clear biphasic solution was cooled to 20° C. The phases were separated and the organic phase was twice extracted with totally 250 mL of ethyl acetate. The combined organic layers were three times washed with totally 225 mL of aqueous NaCl (10% w/w). The resulting organic solution was concentrated and the solvent almost completely removed under reduced pressure at a jacket temperature of maximal 50° C. The residue was dissolved in 250 mL of ethanol where after a part of the solvent (75 mL) was removed again under reduced pressure (ca. 170 mbar) at a jacket temperature of maximal 50° C. The resulting solution was treated with 462.5 mL of ethanol and cooled to 20° C. About 20% (ca. 29.5 mL) of a solution of 11.83 g (63.9 mmol) of dicyclohexylamine in 118 mL of ethanol was added. The mixture was seeded whereupon the product started to precipitate. The suspension was stirred for 1 h at RT and subsequently, the rest of the dicyclohexyl amine solution was slowly added within at least 2 h. The dropping funnel was rinsed with 25 mL of ethanol. The internal temperature was lowered to 0° C. within 4 h where after the suspension was stirred over night at this temperature. The precipitate was filtered with suction, the filter cake was washed with 117.5 mL of cold ethanol (0° C.) and dried under vacuum (50° C., 20 mbar) to afford 35.7 g (yield 82% starting from (S)-3-tert-Butoxy-2-(9H-fluoren-9-ylmethoxycarbonyl-amino)-propionic acid, 96.8% (w/w) purity based on HPLC) of (S,S)-2-[3-tert-Butoxy-2-(9H-fluoren-9-ylmethoxycarbonylamino)-propionyl-amino]-3-hydroxy-propionic acid dicyclohexyl-ammonium salt (3) as a colorless solid.

The HPLC analysis was performed using an external standard of pure (S,S)-2-[3-tert-Butoxy-2-(9H-fluoren-9-ylmethoxycarbonylamino)-propionyl-amino]-3-hydroxy-propionic acid dicyclohexyl-ammonium salt (3). Conditions for HPLC: Column XBridge C18 (Waters), 4.6×150 mm, 3.5 μm; UV detection 206 nm; solutions for gradient: water (A), 20 mM $KH_2PO_4$-buffer, pH 2.5 (B), acetonitrile (C); flow 1.0 mL/min; 20° C.

Gradient:

| T[min] | A[%] | B[%] | C[%] |
| --- | --- | --- | --- |
| 0 | 45 | 15 | 40 |
| 2 | 45 | 15 | 40 |
| 14 | 5 | 15 | 80 |
| 25 | 5 | 15 | 80 |

Retention Times:

(S,S)-2-[3-tert-Butoxy-2-(9H-fluoren-9-ylmethoxycarbonylamino)-propionyl-amino]-3-hydroxy-propionic acid dicyclohexyl-ammonium salt (3) 8.4 min Fmoc-L-Ser(tBu)-OH (1) 11.6 min This HPLC-method results in a value for the assay of the free acid of (3). From this value, the assay of the corresponding dicyclohexylammonium salt is calculated, assuming a stoichiometric ratio of 1:1 of free acid and dicyclohexyl ammonium.

A GC analysis using an internal standard of dodecane is used to measure the content of dicyclohexyl amine. Conditions for GC: Column fused silica, 100% polydimethylsiloxane, 1 μm, L=15 m, ID=0.25 mm; carrier gas hydrogen, pressure: 53 kPa, lin. velocity: 73 cm/s, split-ratio: 1:100.

Temperature Program:

| Heating rate [° C./min] | end-temperature [° C.] | duration of isothermal step at end-temperature [min] |
| --- | --- | --- |
| 0.0 | 40 | 1 |
| 50 | 240 | 5 |
| 0.0 | 320 | 10 |

Retention Times:

Dodecane 4.10 min

Dicyclohexylamine 4.90 min

Example 2

A 500 mL double jacketed glass reactor equipped with a mechanical stirrer, a Pt-100 thermometer, reflux condenser, a dropping funnel with cotton filter, and a nitrogen inlet was charged with 25.0 g (37.0 mmol) of (S,S)-2-[3-tert-Butoxy-2-(9H-fluoren-9-ylmethoxycarbonylamino)-propionylamino]-3-hydroxy-propionic acid dicyclohexylammonium salt (3), 100 mL of tert-butyl methyl ether and a solution of 4.70 g of sulfuric acid (96%) in 44.3 mL of water. The mixture was stirred for 90 minutes at room temperature. The aqueous phase was separated and the organic phase was twice washed with a total of 76 ml of aqueous sodium chloride (0.5%-w/w) and again with 38 mL of water. The organic solvent was completely removed under reduced pressure (500-100 mbar)

and at a jacket temperature of 50° C. The foamy residue was dissolved in 100 mL of tetrahydrofuran and the solvent was again completely removed reduced pressure (500-100 mbar) and at a jacket temperature of 50° C. The residue was dissolved in 450 ml of tetrahydrofuran and the resulting clear solution was treated with 35.4 g (333 mmol) of 2,2-dimethoxy propane and 0.65 g (6.7 mmol) of methanesulfonic acid. The mixture was heated under reflux at a jacket temperature of 85° C. while leading back the distillate over 73 g of molecular sieve (0.4 nm). After 16 h, the slightly yellowish solution was cooled to 20° C. and sampled, and the mixture was treated with 0.828 g (8.14 mmol) of triethylamine and stirred for 10 minutes. The solvent was completely removed under reduced pressure (350-100 mbar) and at a jacket temperature of 50° C. The residue was treated with 100 mL of tert-butyl methyl ether and again completely concentrated under reduced pressure (350-100 mbar) and at a jacket temperature of 50° C. The residue was dissolved in 175 mL of tert-butyl methyl ether and cooled to 20° C. to 25° C. The solution was treated with 87.5 mL of water and stirred for 10 minutes. The phases were separated and the organic phase was completely concentrated under reduced pressure (350-100 mbar) and at a jacket temperature of 50° C. The foamy residue was dissolved in 100 mL of tert-butyl methyl ether and completely concentrated under reduced pressure (350-100 mbar) and at a jacket temperature of 50° C. This step was twice repeated with a total of 200 mL of tert-butyl methyl ether. The residue was dissolved in 45.2 mL of tert-butyl methyl ether at 20° C. to 25° C. and treated with 22.6 mL of Isopropanol. At this temperature, the solution was treated with 175 mL of pentane, seeded, then kept stirring for at least 15 minutes, and again slowly treated with 200 mL of pentane within 1 h. The resulting solution stirred for 4 to 16 h and then cooled to 0° C. within 1-2 h and again stirred for another 2 h at this temperature. The precipitate was filtered with suction, the filter cake washed in two portions with a total of 60 ml of cold pentane (0° C.) and dried under vacuum (50° C., 20 mbar) to afford 14.3 g (yield 75% starting from (S,S)-2-[3-tert-Butoxy-2-(9H-fluoren-9-ylmethoxycarbonylamino)-propionylamino]-3-hydroxy-propionic acid dicyclohexyl-ammonium salt, 98.7% (w/w) purity based on HPLC) of (S,S)-3-[3-tert-Butoxy-2-(9H-fluoren-9-yl-methoxycarbonylamino)-propionyl]-2,2-dimethyl-oxazolidine-4-carboxylic acid (4) as a colorless solid.

The HPLC analysis was performed using an external standard of pure (S,S)-3-[3-tert-Butoxy-2-(9H-fluoren-9-yl-methoxycarbonylamino)-propionyl]-2,2-dimethyl-oxazolidine-4-carboxylic acid (4). Conditions for HPLC: Column XBridge C18 (Waters), 4.6×150 mm, 3.5 μm; UV detection 206 nm; solutions for gradient: water (A), 20 mM $KH_2PO_4$-buffer, pH 2.5 (B), acetonitrile (C); flow 1.0 mL/min; 20° C.

Gradient:

| T[min] | A[%] | B[%] | C[%] |
|---|---|---|---|
| 0 | 27 | 15 | 58 |
| 1 | 27 | 15 | 58 |
| 6 | 20 | 15 | 65 |
| 10 | 5 | 15 | 80 |
| 20 | 5 | 15 | 80 |
| 20.1 | 70 | 15 | 15 |
| 25 | 70 | 15 | 15 |

Retention Times:
(S,S)-3-[3-tert-Butoxy-2-(9H-fluoren-9-yl-methoxycarbonylamino)-propionyl]-2,2-dimethyl-oxazolidine-4-carboxylic acid (4) 7.3 min
(S,S)-2-[3-tert-Butoxy-2-(9H-fluoren-9-ylmethoxycarbonylamino)-propionyl-amino]-3-hydroxy-propionic acid dicyclohexyl-ammonium salt (3) 3.0 min Fmoc-L-Ser (tBu)-OH (1) 5.6 min Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A process for the manufacture of the compounds of formula I:

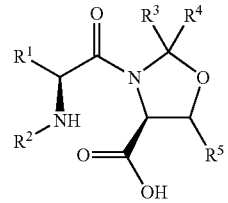

wherein: (1) $R^1$ is a side chain of an alpha amino acid, (2) $R^2$ is an amino protecting group, (3) $R^3$ and $R^4$ are independently either hydrogen or a $C_{1-4}$-alkyl, and (4) $R^5$ is hydrogen or methyl;
wherein said process comprises the following steps:
(a) reacting an amino acid derivative of formula II:

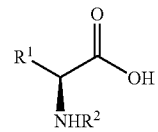

wherein $R^1$ and $R^2$ are as defined previously,
with serine or threonine to obtain a dipeptide of formula III:

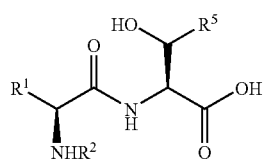

wherein $R^1$, $R^2$ and $R^5$ are as defined previously;
(b) adding the amine of formula V:

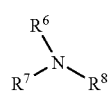

wherein $R^6$, $R^7$ and $R^8$ are independently selected from the group consisting of hydrogen, a $C_{1-4}$-alkyl and a $C_{3-7}$-cycloalkyl, with the proviso that not all of $R^6$, $R^7$ and $R^8$ are hydrogen;

to form the ammonium salt of the dipeptide of formula III in crystal form:

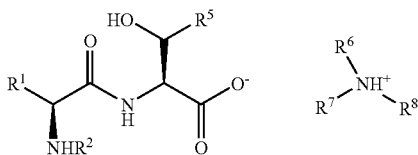

wherein $R^1$, $R^2$, $R^5$, $R^6$, $R^7$ and $R^8$ are as defined previously;

(c) adding an acid to the ammonium salt in step (b) to release the free acid of the dipeptide of formula III from the ammonium salt, and removing the protonated amine from the reaction mixture; and (d) effecting the ring closure of the free acid of the dipeptide of formula III in step (c) with a compound selected from the group consisting of:

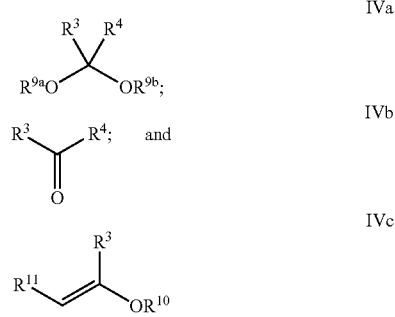

wherein: (1) $R^3$ and $R^4$ are independently either hydrogen or a $C_{1-4}$-alkyl, with the proviso that not both $R^3$ and $R^4$ are hydrogen, (2) $R^{9a}$ and $R^{9b}$ are independently a $C_{1-4}$-alkyl, (3) $R^{10}$ is a $C_{1-4}$-alkyl, a $C_{1-4}$-alkanoyl or an aryl, and (4) $R^{11}$ is hydrogen or a $C_{1-3}$-alkyl, in the presence of an acidic catalyst to obtain compounds of formula I.

2. The process of claim 1, wherein $R^1$ is a side chain selected from the group consisting of: valine, leucine, isoleucine, methionine, phenylalanine, asparagine, glutamine, glutamic acid, histidine, lysine, arginine, aspartic acid, alanine, serine, threonine, tyrosine, tryptophan, cysteine, glycine, aminoisobutyric acid, and proline.

3. The process of claim 1, wherein $R^2$ is selected from the group consisting of: Fmoc, Cbz, Moz, Boc, Troc, Teoc, and Voc.

4. The process of claim 1, wherein the amino acid derivative of formula II is activated with an activating reagent prior to reacting it with serine or threonine.

5. The process of claim 4, wherein the activating reagent is selected from the group consisting of: DIC/HOSu, DIC/Pentafluorphenol, DIC/HOBt, DCC/HOSu, DCC/Pentafluorphenol, DCC/HOBt, EDC (xHCl)/HOSu, and HBTU/HOBt.

6. The process of claim 4, wherein the activating reagent is DIC/HOSu.

7. The process of claim 1, wherein the ratio of serine or threonine to amino acid derivative of formula I is selected in the range of 1.5 to 3.0 to 1.

8. The process of claim 1, wherein $R^6$, $R^7$ and $R^8$ are independently selected from the group consisting of hydrogen, ethyl and cyclohexyl.

9. The process of claim 1, wherein the amine of formula V is dicyclohexylamine.

10. The process of claim 1, wherein the crystallization in step (b) takes place in an organic solvent selected from the group consisting of: methanol, ethanol, n-propanol, i-propanol, ethylacetate, and tetrahydrofuran.

11. The process of claim 1, wherein the free acid of the ammonium salt of formula III in step (c) is released in the presence of a mineral acid, taken up in an organic solvent while the amine is removed by extraction with water and/or an aqueous solution of a mineral salt.

12. The process of claim 1, wherein the ring closure in step (d) is effected with 2,2-dimethoxypropan, 2-methoxypropen or 2-acetoxypropen.

13. The process of claim 1, wherein the ring closure in step (d) is effected with 2,2-dimethoxypropan.

14. The process of claim 1, wherein the acidic catalyst for the ring closure in step (d) is selected from the group consisting of methane sulfonic acid, (+) camphor-10-sulfonic acid, p-toluenesulfonic acid, and pyridinium p-toluenesulfonate.

15. The process of claim 1, wherein the ring closure in step (d) is effected in the presence of an organic solvent.

* * * * *